United States Patent
Grajales et al.

(10) Patent No.: US 7,976,480 B2
(45) Date of Patent: Jul. 12, 2011

(54) WEARABLE AUSCULTATION SYSTEM AND METHOD

(75) Inventors: Lillana Grajales, Bloomingdale, IL (US); Mark W. Cholewczynski, Wheaton, IL (US); Mark A. Krizik, Homer Glen, IL (US); Lawrence E. Lach, Chicago, IL (US); Ion V. Nicolasescu, Carpentersville, IL (US)

(73) Assignee: Motorola Solutions, Inc., Schaumburg, IL (US)

( * ) Notice: Subject to any disclaimer, the term of this patent is extended or adjusted under 35 U.S.C. 154(b) by 1439 days.

(21) Appl. No.: 11/008,430

(22) Filed: Dec. 9, 2004

(65) Prior Publication Data

US 2006/0129067 A1   Jun. 15, 2006

(51) Int. Cl.
*A61B 7/00* (2006.01)

(52) U.S. Cl. .................. 600/586; 600/528; 381/67

(58) Field of Classification Search ............ 128/920; 600/300, 301, 528, 586, 525; 181/131; 381/67
See application file for complete search history.

(56) References Cited

U.S. PATENT DOCUMENTS

| | | | |
|---|---|---|---|
| 5,853,005 A | 12/1998 | Scanlon | |
| 5,990,793 A | 11/1999 | Bieback | |
| 6,080,690 A | 6/2000 | Lebby et al. | |
| 6,121,881 A | 9/2000 | Bieback et al. | |
| 6,229,762 B1 * | 5/2001 | Fisher et al. | 367/149 |
| 6,478,744 B2 * | 11/2002 | Mohler | 600/485 |
| 6,606,993 B1 | 8/2003 | Wiesmann et al. | |
| 6,661,897 B2 | 12/2003 | Smith | |
| 6,852,084 B1 * | 2/2005 | Boesen | 600/528 |
| 2002/0188227 A1 * | 12/2002 | Chong et al. | 600/586 |
| 2003/0055359 A1 * | 3/2003 | Halleck et al. | 600/586 |
| 2004/0032957 A1 * | 2/2004 | Mansy et al. | 381/67 |
| 2004/0087865 A1 | 5/2004 | Kelly | |
| 2004/0096069 A1 | 5/2004 | Chien | |
| 2004/0138580 A1 | 7/2004 | Frei et al. | |
| 2004/0148109 A1 | 7/2004 | Fischer | |
| 2004/0249633 A1 * | 12/2004 | Asseily et al. | 704/200 |
| 2005/0124902 A1 * | 6/2005 | Baumer et al. | 600/509 |
| 2006/0047215 A1 * | 3/2006 | Newman et al. | 600/513 |

OTHER PUBLICATIONS

PCT International Search Report Dated Mar. 28, 2006.
Michael V. Scanlon, Acoustic Sensor for Health Status Monitoring; Jan. 1, 1998; US Army Research Laboratory; 19 Pages.

(Continued)

*Primary Examiner* — Max Hindenburg
*Assistant Examiner* — Jonathan M Foreman
(74) *Attorney, Agent, or Firm* — Valerie M. Davis (57) ABSTRACT

A method and system for monitoring physiological parameters is useful for remote auscultation of the heart and lungs. The system includes an acoustic sensor (105) that has a stethoscopic cup (305). A membrane (325) is positioned adjacent to a first end of the stethoscopic cup (305), and an impedance matching element (335) is positioned adjacent to the membrane (325). The element (335) provides for acoustic impedance matching with a body such as a human torso. A microphone (315) is positioned near the other end of the stethoscopic cup (305) so as to detect sounds from the body. A signal-conditioning module (110) is then operatively connected to the acoustic sensor (105), and a wireless transceiver (115) is operatively connected to the signal-conditioning module (110). Auscultation can then occur at a remote facility that receives signals sent from the transceiver (115).

20 Claims, 7 Drawing Sheets

OTHER PUBLICATIONS

Michael V. Scanlon, "Acoustic Sensor Array Extracts Physiology During Movement"; US Army Research Laboratory, Adelphi, MD; Visualization of Temporal and Spatial Data for Civvillian and Defense Applications; Proceedings of SPIE; vol. 4368; 2001; 12 Pages.

M.T. Pourazad, et al. "Heart Sound Cancellation From Lung Sound Recordings Using Adaptive Threshold and 2D Interpolation in Time-Frequency Domain", Proceedings of the 25th Annual International Conference of the IEEE EMBS; Cancun, Mexico; Sep. 17-21, 2003; pps 2586-2589.

* cited by examiner

WEARABLE AUSCULTATION SYSTEM AND METHOD

FIELD OF THE INVENTION

The present invention relates generally to a method and system for monitoring physiological parameters, and in particular, although not exclusively, to remote auscultation of the heart and lungs.

BACKGROUND OF THE INVENTION

Occupations such as firefighting and police work often require personnel to perform under extreme physical and mental stress. Real time physiological monitoring of such personnel can be a useful tool for recognizing when personnel are in danger of exceeding their physical limits. Physiological parameters such as heart rate, heart rate variability (HRV) and respiration provide early warning signs of high stress that can be used to protect health and safety. However, existing devices for measuring such parameters are generally bulky, uncomfortable to wear, and not effective for occupational monitoring.

A government study on firefighter fatality showed that 50% of firefighter deaths are caused by heart attacks. Thus, monitoring a firefighter's vital signs during and after high-stress missions can assist in preventing heart attacks or in providing immediate medical attention when it is determined that a firefighter is close to having a heart attack. Further, police officers are known to have over twice the incidence of cardiovascular disease as the general population. A study determined that being employed in law enforcement places one at a greater risk of developing cardiovascular disease than having high blood pressure, having diabetes, being overweight, or being a smoker. Unlike firefighters, whose heart rates increase mainly from physical stress, in police officers unhealthy heart rate increases are often due to emotional stress. Nevertheless, as in the case of firefighters, heart rate monitoring of police officers can also improve health and safety. For example, a command center can be alerted when an officer has been exposed to a high stress situation for too long. Real time physiological monitoring of police and firefighter personnel can also assist in training and self-evaluation.

Among the most important vital signs that can indicate impending heart attacks are heart rate and HRV. Changes in beat-to-beat heart rate determine HRV. In general, a higher HRV is desirable; lower HRV has been found to be a significant predictor of cardiac mortality and morbidity. By evaluating HRV it is often possible to assess a person's heart performance and the onset of a heart malfunction.

An effective real time physiological monitoring system for high stress occupational environments must satisfy numerous criteria. It must be comfortable to wear, low-weight, passive, and robust. Preferably, such a system should also conform well to a person's existing clothing and equipment.

Auscultation is a class of methods used to listen to the sounds of the body during a physical examination and is widely recognized as an important diagnostic tool. Auscultation is most commonly performed by listening through a stethoscope, where a medical professional may auscultate a patient's lungs, heart, and intestines to evaluate the frequency, intensity, duration, number, or quality of sounds. But generally such procedures are performed in a controlled and quiet environment such as in a clinic or hospital. Standard stethoscopes are thus not designed for and are not effective at monitoring heart and respiratory parameters over extended periods in harsh occupational environments.

Prior art devices for measuring heart rate and respiration, including stethoscopes, generally require direct contact with the skin. Other common physiological sensors include electrodes or small microphones that are adhered directly to the skin with tape or wrappings. Electrodes measure the electrical impulses associated with physiological parameters; whereas microphones detect the sound of organs such as the heart and lungs. Wires leading from these sensors are then generally connected to some form of data acquisition device or data transceiver. Disadvantages of these devices include the fact that they require additional time and effort to attach to the body. Such time requirements can be particularly problematic for emergency response personnel who already are required to outfit themselves with sophisticated equipment, such as breathing apparatuses, in very limited time periods. Further, wiring from such prior art devices can be uncomfortable and can impede movement.

BRIEF DESCRIPTION OF THE DRAWINGS

A preferred embodiment of the invention is now described, by way of example only, with reference to the accompanying figures in which.

DETAILED DESCRIPTION OF THE PREFERRED EMBODIMENTS

While this invention is susceptible of embodiments in many different forms, there are shown in the figures and will herein be described in detail specific embodiments, with the understanding that the present disclosure is to be considered as an example of the principles of the invention and not intended to limit the invention to the specific embodiments shown and described. Further, the terms and words used herein are not to be considered limiting, but rather merely descriptive. It will also be appreciated that for simplicity and clarity of illustration, elements shown in the figures have not necessarily been drawn to scale. For example, the dimensions of some of the elements are exaggerated relative to each other. Further, where considered appropriate, reference numerals have been repeated among the figures to indicate corresponding elements.

Figure 1:
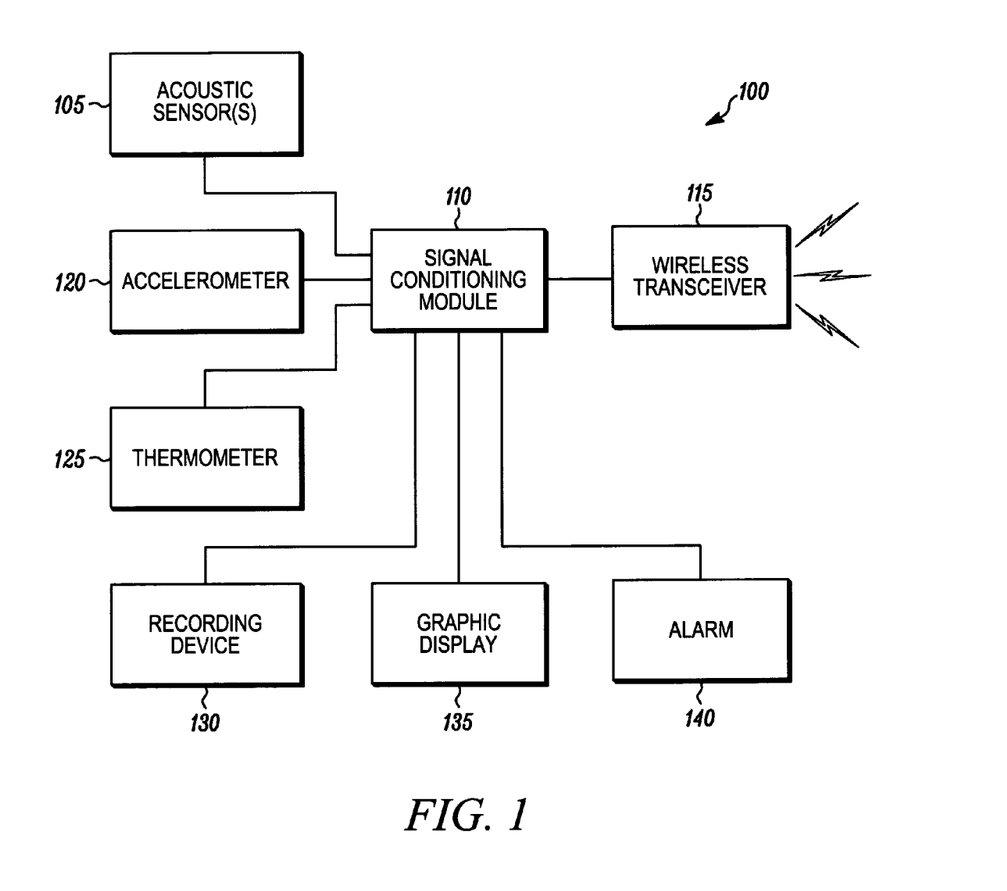
FIG. 1 is a block diagram illustrating the elements of a wearable physiological monitoring system according to an embodiment of the present invention.

Referring to FIG. 1, there is a schematic diagram illustrating the elements of a wearable physiological monitoring system 100 according to one embodiment of the present invention. The system 100 includes at least one wearable acoustic sensor 105, a signal-conditioning module 110, and a wireless transceiver 115. Acoustic signals from a body, such as the torso of a human, are detected by the sensor 105. The signals are then processed by the signal conditioner 110. Finally, conditioned signals are transmitted wirelessly to a receiving station (not shown) using the transceiver 115. Other sensors such as an accelerometer 120 and thermometer 125 may also be incorporated into the system 100. Other optional output devices such as a recording device 130, a graphical display 135, and an alarm 140 are also shown in FIG. 1.

The system 100 thus enables remote, real-time auscultation of various vital parameters of personnel that are experiencing high-stress. A remote command center, for example, can monitor firefighters in a burning building and determine instantly when a particular firefighter needs assistance, or when a shift of firefighters should be rotated away from a hazardous environment because of extreme stress. Similarly, the real-time health of personnel in other hazardous occupations such as law enforcement, mining, diving, and the military can be monitored remotely. The effects of high stress and extreme exhaustion, such as heart attacks and collapse, can therefore be avoided or remedied through remote auscultation. Such remote auscultation may further benefit others such as athletes in training and people with fragile health including the very young and the elderly. Other conditions such as the onset of sleep can also be detected through such remote auscultation.

Figure 2:
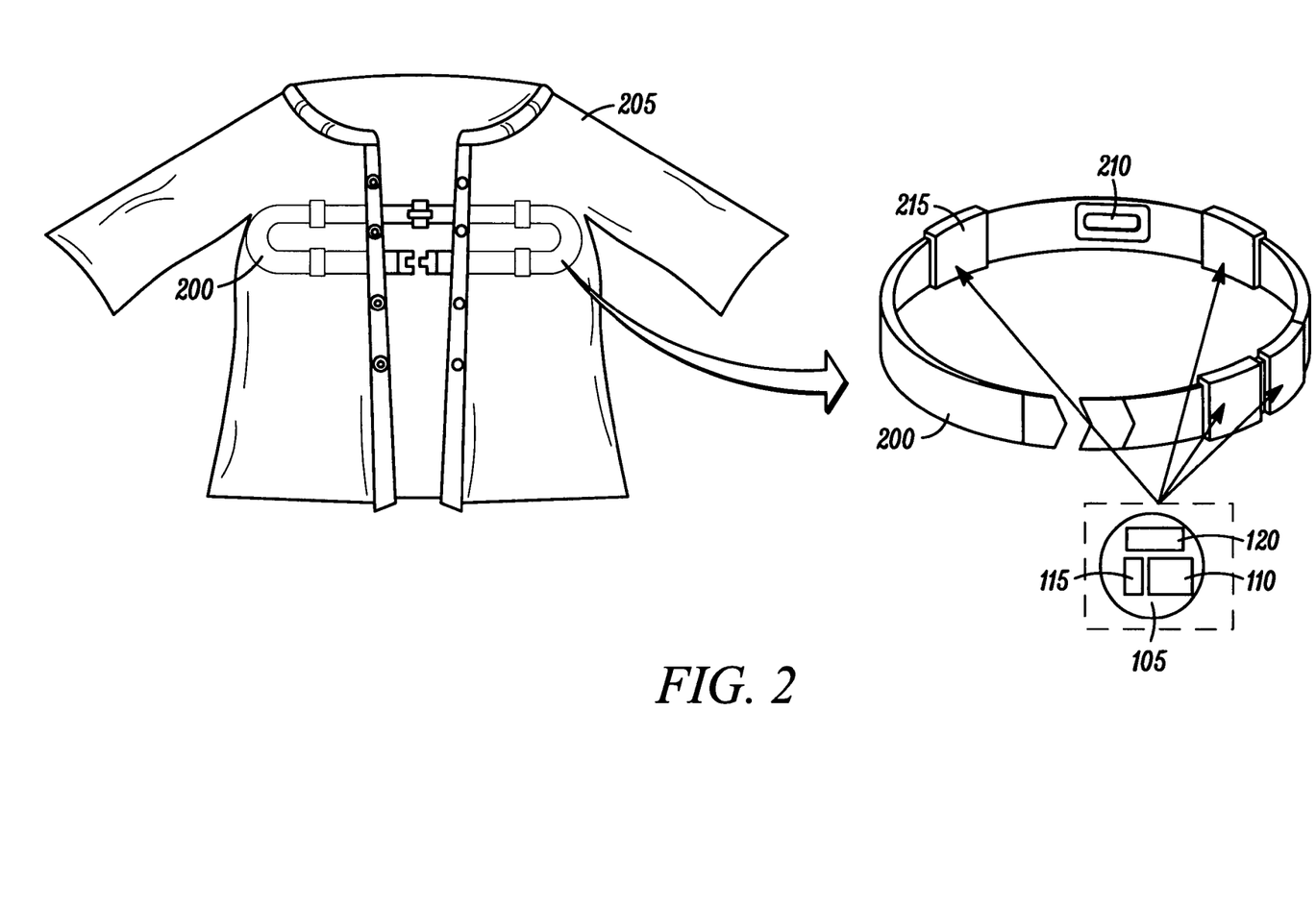
FIG. 2 is a schematic diagram illustrating a wearable harness according to an embodiment of the present invention.

Referring to FIG. 2, there is a schematic diagram illustrating a wearable harness 200 that incorporates the system 100 according to a specific embodiment of the present invention. The harness 200 is designed to be removably attached to clothing such as a firefighter's jacket 205. A loop 210 at the back of the harness 200 enables secure attachment of the harness 200 to the jacket 205. The harness 200 includes multiple acoustic sensors 105, and additional devices such as accelerometers 120, signal conditioning modules 110, and transceivers 115. When worn by a person, some of the sensors 105 are located near the person's back, for example to measure respiratory sounds, and other sensors are located near the person's chest, for example to measure cardiologic sounds. Other sensors, such as a respiration sensor 215 attached to a back portion of the harness 200, also may be incorporated into the harness 200. As described in more detail below, the mechanical design of the sensors 105 enables the acoustic signals from the organs of a body to be detected through clothing while maintaining an acceptable signal to noise ratio (SNR). Prior art physiological acoustic sensors designed for occupational monitoring have generally required direct contact with the skin in order to achieve an acceptable SNR.

Figure 3:
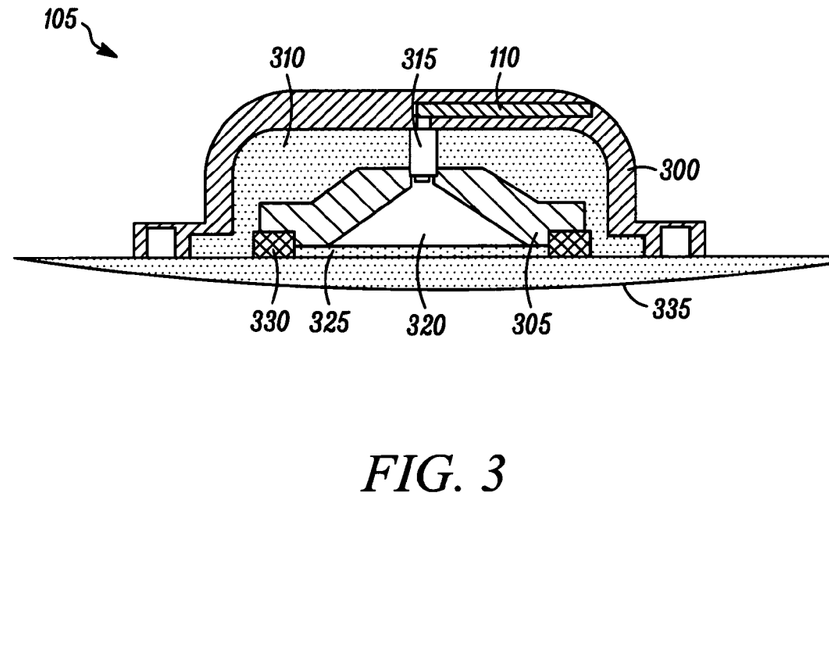
FIG. 3 is a cross sectional view of an acoustic sensor according to an embodiment of the present invention.

Referring to FIG. 3, there is a cross sectional view of an acoustic sensor 105 according to an embodiment of the present invention. The sensor 105 includes a housing 300 and a stethoscopic cup 305 inside of the housing 300. An insulating material 310 fills a cavity between the housing 300 and the stethoscopic cup 305 in order to insulate the cup 305 from external noise that may penetrate the housing 300. A microphone 315 is positioned at a second end of the cup 305 adjacent the insulating material 310. The cup 305 may be structured to form a conical cavity 320 and the microphone 315 is generally located near the vertex of the conical cavity 320. A membrane 325 is positioned at a first end of the stethoscopic cup 305 and forms a base of the conical cavity 320. The membrane 325 may be attached to the cup 305 using a circular flange 330. An acoustic impedance matching element 335 is positioned adjacent to the membrane 325. Finally, the wireless transceiver 115 and the signal-conditioning module 110 are electrically connected to the microphone 315 and may be attached to the housing 300 using any suitable means.

The acoustic impedance matching element 335 is designed to maximize the transfer of acoustic signal energy from a body to the sensor 105. That may be best achieved when the acoustic impedance of the sensor matches the acoustic impedance of the body. Those skilled in the art know that the specific acoustic impedance of a material is the product of the density and acoustic velocity of that material. Sound waves are reflected at material boundaries that define differences in specific acoustic impedance, and such reflections result in a loss of transmission energy. Thus, by approximately matching the density and acoustic velocity of the acoustic impedance matching element 335 with an average density and acoustic velocity of a human torso, the present invention is able to maximize the transfer of acoustic signal energy from organs in the torso to the sensor 105. The acoustic impedance matching element 335 may comprise for example a solid material that is molded to conform to the shape of the torso or may comprise a flexible pouch that is filled with an aqueous, gelatinous or elastic material. Sound conductive gels that work effectively in some embodiments of the present invention include Aquasonic (Registered Trademark) gels manufactured by the RP Kincheloe Company.

Because direct skin contact is not required, various alternative designs of the present physiological monitoring system 100 are made possible, which are comfortable to wear and appropriate for various occupational conditions. For example, the system 100 can be incorporated into jackets and vests that are generally worn over undergarments such as T-shirts. The present physiological monitoring system may likewise be attached to an article of clothing such as, for instance, bulletproof vests, fire retardant jackets, diving suits, law enforcement uniforms, military uniforms, mining uniforms, athletic uniforms, trousers, patient gowns, clothing for children and the elderly, etc. The harness design 200 described above is an example of one such design and other designs are described in more detail below.

Figure 4:
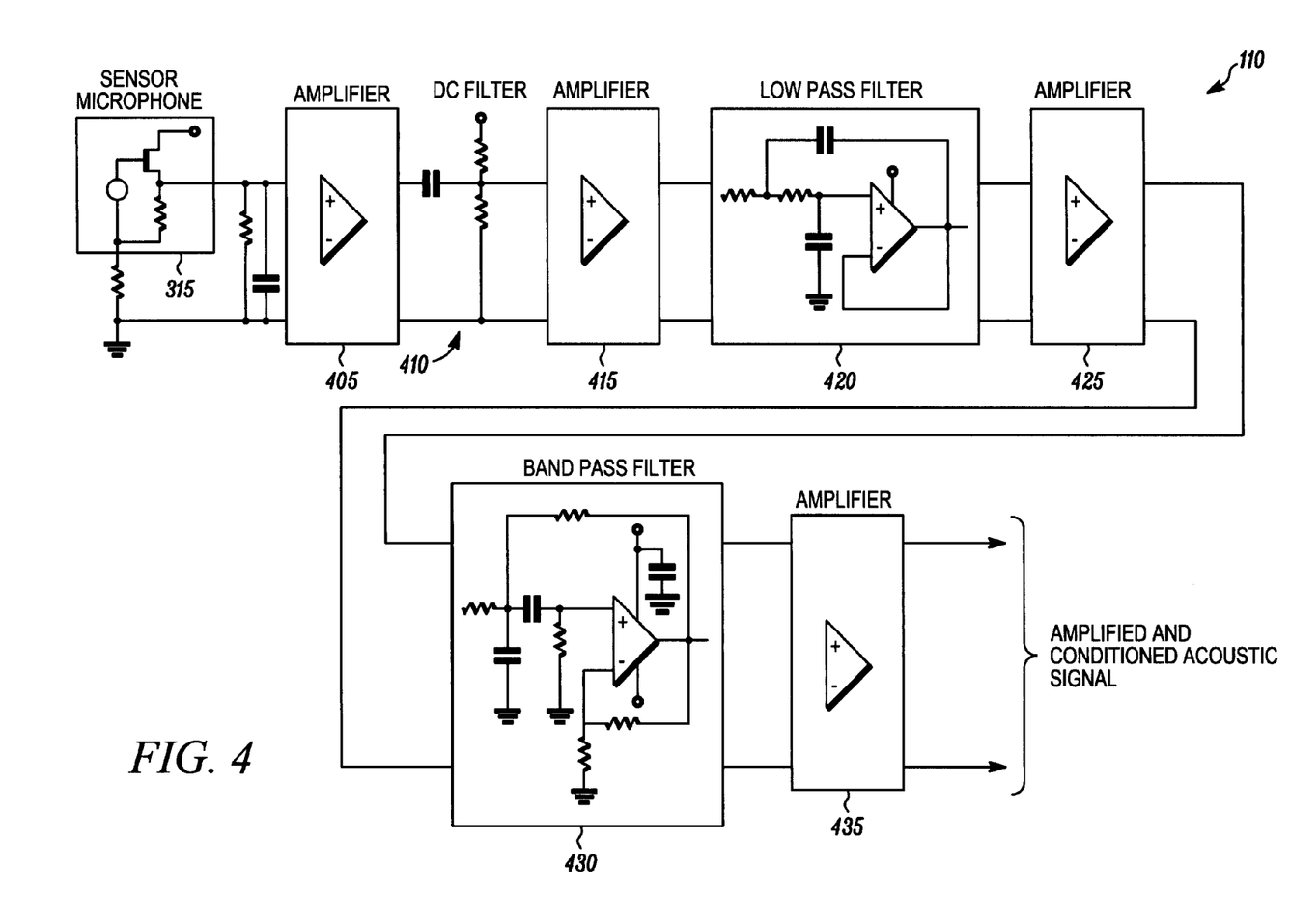
FIG. 4 is a schematic circuit diagram of components of a typical signal-conditioning module according to an embodiment of the present invention.

Referring to FIG. 4, there is illustrated a schematic circuit diagram of components of a signal-conditioning module 110 according to one embodiment of the present invention. A microphone 315 in a sensor 105 first converts the sound energy received from a body into an electrical signal. The electrical signal is then amplified in a first amplifier 405. The signal is then improved using a DC filter 410 and a second amplifier 415. A low-pass filter 420 is then used to eliminate most high-frequency signals that could not reasonably form part of the relatively low-frequency physiological parameters of interest such as heart and respiratory parameters. For example, a reasonable cut-off frequency for the low-pass filter 420 is 80 Hz for heart sounds or 1500 Hz for respiration sounds. The filtered signal is then amplified again using a third amplifier 425. Next, the signal is passed through a high-gain, band-pass filter 430 that targets only a particular physiological parameter of interest. Finally, the signal is amplified in a fourth amplifier 435.

For example, for measuring heart rate or HRV, the band-pass filter 430 of the signal-conditioning module 110 is tuned to select only the main first and second (S1 and S2) heart sounds. The S1 is the most prominent beat of the ventricle contraction (systole) and the S2 is the atrium contraction (diastole). These are the "lub-dup" sounds that comprise the heartbeat and are produced when the heart valves close. The major concentration of energy from these sounds is generally below 150 Hz. A similar strategy that targets specific lung sounds is used for measuring respiratory parameters. For example, lung sounds may be targeted in a frequency band of 70 to 2000 Hz.

Additional sensors such as the accelerometer 120 and thermometer 125 shown in FIG. 1 may be used in conjunction with the acoustic sensors 105. The accelerometer 120 can assist in conditioning the system 100 to filter noise associated with rapid gross movement of a person wearing the system 100. Various types of small accelerometers, such as 2-D piezoelectric accelerometers, may be incorporated into the acoustic sensors 105 or into the signal-conditioning module 110. A thermometer 125 may be used in situations where temperature extremes place personnel at hyperthermic or hypothermic risk, such as, respectively, high-heat in fire fighting and some mining operations, and cold in some diving and rescue operations.

The signal-conditioning module 110, recording device 130, graphic display 135, and alarm 140 can be incorporated into a local system 100 that is worn by a user. However, in order to save on weight and complexity, amplified raw signals from a sensor 105 may also be transmitted directly from a wireless transceiver 115, where additional signal-conditioning and calculations then occur at a remote site.

Figure 5:
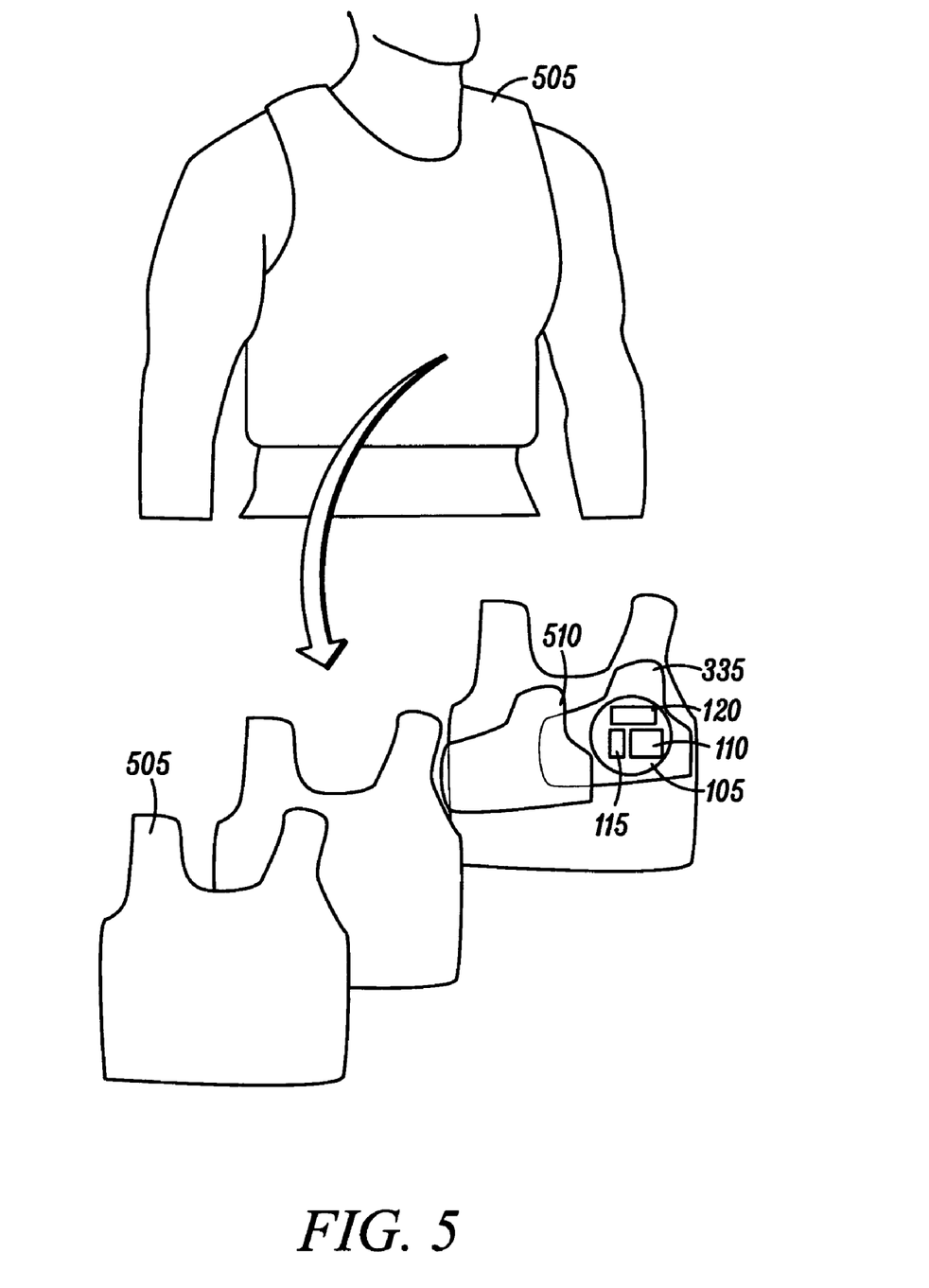
FIG. 5 is a schematic diagram illustrating a further embodiment of the present invention incorporated into a vest.

Referring to FIG. 5, there is a schematic diagram illustrating a further embodiment of the present invention incorporated into a vest 505. Here, a sensor 105 and wireless transceiver 115, among other instrumentation, are incorporated into the vest 505 on top of a relatively large-area acoustic impedance matching element 335. A foam pad 510 is then, ideally, placed on top of the instrumentation to protect it from external forces and impacts and to insulate it from outside noise—thereby increasing the sensitivity of the sensor 105. One material that may be used for the foam pad 510 is Dow Corning's 3-8109 Silicone Foam. The physiological monitoring system 100 of the present invention therefore may be incorporated into existing occupational clothing, such as bulletproof vests worn by police officers. The armor protection of a bulletproof vest may be included in the multiple plys of the vest 505.

In addition to transmitting a signal from the system 100 to a remote facility for auscultation purposes, other embodiments of the present invention may include various other output devices. For example, referring again to FIG. 1, an embodiment of the present invention may include a recording device 130, a graphical display 135 or an alarm 140. A recording device 130 may be useful to a user for later analysis of heart and lung performance, for example during athletic training. A graphical display 135 and an alarm 140 may be useful for informing a user about respiration and heart rate levels, and for alerting users whenever certain physiological parameters reach dangerous levels.

Figure 6:
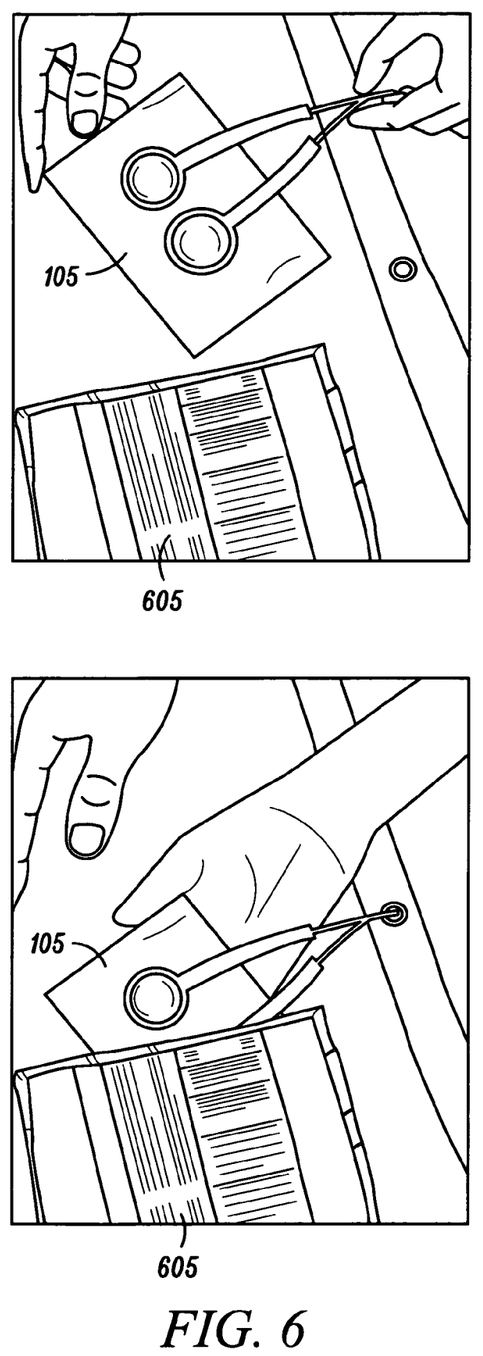
FIG. 6 is a schematic diagram illustrating the use of an inner clothing pocket designed to receive components of a physiological monitoring system according to an embodiment of the present invention.

Referring to FIG. 6, there is a schematic diagram illustrating the use of an inner clothing pocket 605 designed to receive components of a physiological monitoring system 100 of the present invention. Designing the system 100 to be easily inserted and removed from a pocket 605, significantly improves the versatility of occupational clothing that is used in conjunction with the invention. For example, such a system 100 can be quickly removed when it is not needed for a particular mission, when it requires servicing, when the clothing requires washing, or when a wearer needs to switch the system 100 into another item of clothing. The inner lining of the pocket 605 may be made of a thin mesh to minimize the sound dampening associated with textiles. Also, the acoustic impedance matching element 335 may be separated from a sensor 105 and attached independently to the pocket 605, thus minimizing the material between the body and the sensor 105 and improving the fit of the impedance matching element to the body.

The wireless transceiver 115 of the present invention may be of various types, including adaptations of standard two-way radios used by police and fire personnel. Incorporating the communications requirements of the present invention into multi-function voice communication devices, already worn by a user, thus further increases the convenience and comfort of the present system 100 and reduces weight and complexity. The required power of a transceiver 115 varies depending on the needs of a particular system 100. For example, systems 100 designed for firefighters may need only communicate over short distances that are required to reach a local command unit operating from a nearby truck. Other systems 100 may require relaying of signals over longer distances or onto the Internet for remote monitoring by a permanent base station.

Figure 7:
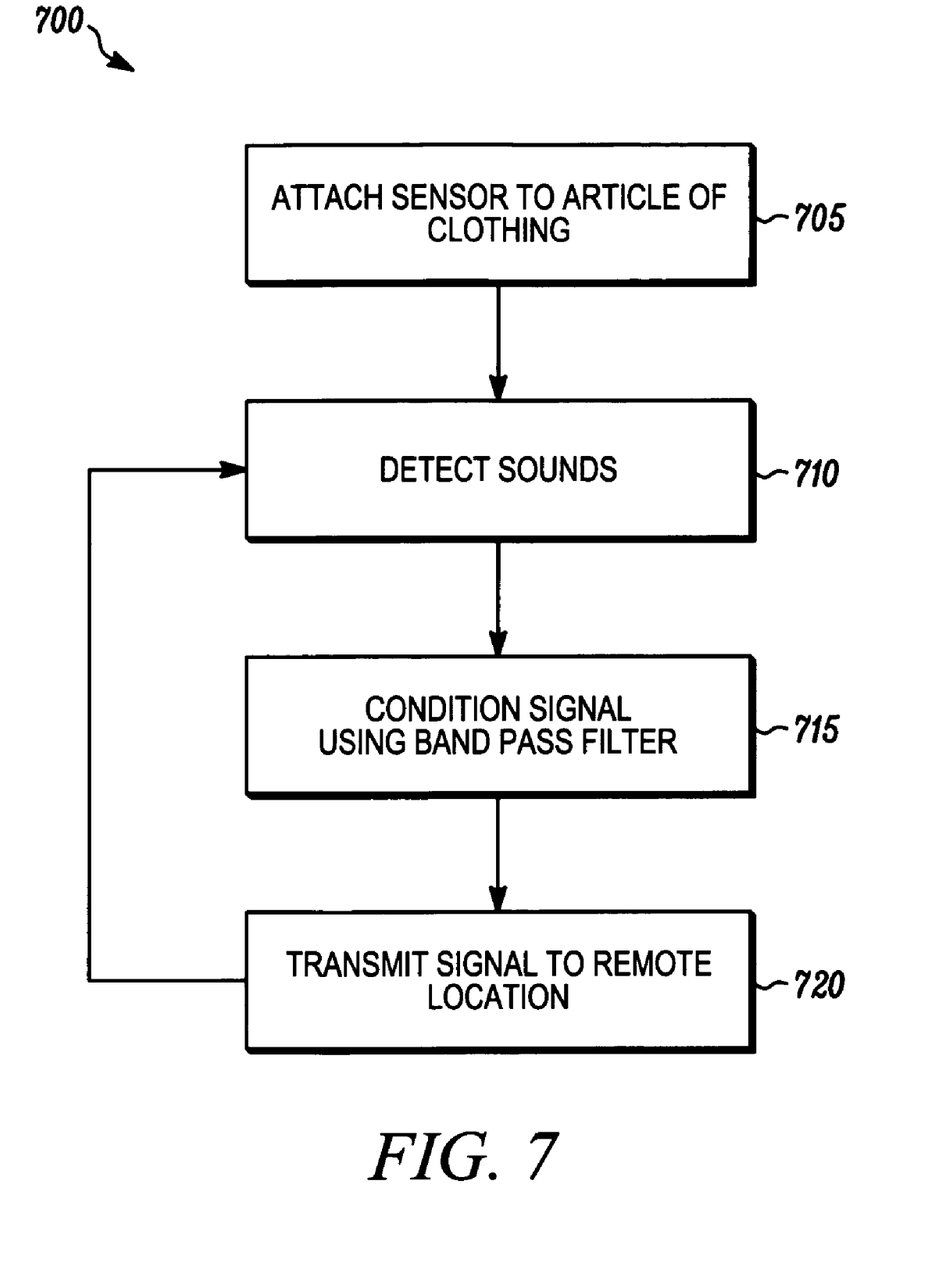
FIG. 7 is a general flow diagram illustrating a method for remote auscultation according to an embodiment of the present invention.

Referring to FIG. 7, there is a general flow diagram illustrating a method 700 for transmitting signals for remote auscultation according to an embodiment of the present invention. The method 700 begins at step 705 where a sensor 105 is attached to an article of clothing. The sensor 105 may include the elements described above including an acoustic impedance matching element 335. Next, at step 710 sounds are detected within the body using the sensor 105 and are converted to an electrical signal. At step 715, the signal is conditioned using a band pass filter 430 tuned to the frequency of a particular body organ. Then at step 720 the signal is transmitted to a remote location where a condition of the body may be assessed. Finally, the method 700 returns to step 710 where additional sounds are detected.

In summary the present invention includes a wearable auscultation system 100 and method 700 for real time, remote monitoring and auscultation of various physiological parameters. An improved sensor design enables sounds from organs in a body to be effectively transmitted through clothing to an impedance matching element 335 that approximately matches the acoustic impedance of the body. The invention can therefore be adapted to existing clothing and uniforms so that it is comfortable and convenient to wear. Multiple sensors 105 may be integrated into the system 100 to simultaneously measure multiple physiological parameters such as heart and respiration rates. Each sensor 105 may be tuned to the specific sounds of a particular organ using band pass filters 430. Further, conditioned signals from the sensors 105 may be communicated to a remote location using existing voice communications equipment already worn by a user, thereby minimizing the weight and complexity of the invention.

The above detailed description provides a preferred exemplary embodiment only, and is not intended to limit the scope, applicability, or configuration of the present invention. Rather, the detailed description of the preferred exemplary embodiment provides those skilled in the art with an enabling description for implementing the preferred exemplary embodiment of the invention. It should be understood that various changes can be made in the function and arrangement of elements and steps without departing from the spirit and scope of the invention as set forth in the appended claims.

We claim:

1. A wearable system for remote auscultation comprising:
   an acoustic sensor comprising:
   a stethoscopic cup having first and second ends;
   a membrane positioned adjacent to the first end of the stethoscopic cup;
   a separate impedance matching element positioned external to the membrane and the stethoscopic cup and adjacent to the membrane, the element providing for acoustic impedance matching with a body; and a microphone positioned near the second end of the stethoscopic cup;

a signal-conditioning module operatively connected to the acoustic sensor; and a wireless transceiver operatively connected to the signal-conditioning module.

2. The system according to claim 1 further comprising a plurality of acoustic sensors, wherein a signal from each sensor of the plurality of sensors is tuned using a band pass filter to detect at least one of heart sounds and lung sounds.

3. The system according to claim 1, wherein the system is attached to an article of clothing.

4. The system according to claim 3, wherein the article of clothing is selected from the group consisting of bulletproof vests, fire retardant jackets, diving suits, law enforcement uniforms, military uniforms, mining uniforms, athletic uniforms, trousers, patient gowns, and clothing for children and the elderly.

5. The system according to claim 1, wherein the system is inserted into a pocket of an article of clothing.

6. The system according to claim 1, wherein the impedance matching element is a pouch filled with one of aqueous, gelatinous, and elastic material.

7. The system according to claim 1, wherein the impedance matching element is a solid that conforms to the shape of a body.

8. The system according to claim 1, wherein the system is integrated into a harness that is wearable by a user.

9. The system according to claim 1, wherein the wireless transceiver is integrated into a multi-function voice communication device.

10. The system according to claim 1 further comprising at least one additional monitoring sensor operatively connected to the signal-conditioning module.

11. The system according to claim 10, wherein the at least one additional monitoring sensor is selected from the group consisting of an acoustic sensor, an accelerometer, and a thermometer.

12. The system according to claim 1 further comprising at least one output device operatively connected to the signal-conditioning module, wherein the at least one output device is selected from the group consisting of a recording device, a graphical display, and an alarm.

13. A method for transmitting signals for remote auscultation comprising the steps of:

attaching a sensor to an article of clothing, wherein the sensor includes a stethoscopic cup having first and second ends, a membrane positioned adjacent to the first end of the stethoscopic cup, a separate impedance matching element positioned external to the membrane and the stethoscopic cup and adjacent to the membrane, the element providing for acoustic impedance matching with a body, and a microphone positioned near the second end of the stethoscopic cup;

detecting sounds within the body using the sensor; and transmitting a signal corresponding to the sounds to a remote location, whereby a condition of the body may be assessed.

14. The method according to claim 13 further comprising the step of conditioning the signal using a band pass filter tuned to the frequency of a body organ prior to transmitting the signal.

15. The method according to claim 13, wherein the step of attaching the sensor to an article of clothing comprises inserting the sensor into a pocket of the article of clothing.

16. The method according to claim 13, wherein the impedance matching element is a pouch filled with one of aqueous, gelatinous, and elastic material.

17. The method according to claim 13, wherein the impedance matching element is a solid that conforms to the shape of a body.

18. The method according to claim 13, wherein the signal is transmitted to the remote location using a wireless transceiver.

19. The method according to claim 18, wherein the wireless transceiver is integrated into a multi-function voice communication device.

20. A system for remote auscultation comprising:

means for attaching a sensor to an article of clothing, wherein the sensor includes a stethoscopic cup having first and second ends, a membrane positioned adjacent to the first end of the stethoscopic cup, a separate impedance matching element positioned external to the membrane and the stethoscopic cup and adjacent to the membrane, the element providing for acoustic impedance matching with a body, and a microphone positioned near the second end of the stethoscopic cup;

means for detecting sounds within the body using the sensor; and means for transmitting a signal corresponding to the sounds to a remote location, whereby a condition of the body may be assessed.

* * * * *